(12) United States Patent
Uhrenius et al.

(10) Patent No.: US 7,054,688 B1
(45) Date of Patent: May 30, 2006

(54) HEART STIMULATOR WITH EVOKED RESPONSE DETECTOR AND AN ARRANGEMENT FOR DETERMINING THE STIMULATION THRESHOLD

(75) Inventors: Åsa Uhrenius, Stockholm (SE); Berit Larsson, Danderyd (SE); Göran Budgifvars, Spånge (SE); Peter Andersson, Sollentuna (SE); Feresteh Shojaei, Solna (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 09/719,739

(22) PCT Filed: Jun. 9, 1999

(86) PCT No.: PCT/SE99/01018

§ 371 (c)(1),
(2), (4) Date: Nov. 17, 2003

(87) PCT Pub. No.: WO99/65566

PCT Pub. Date: Dec. 23, 1999

(30) Foreign Application Priority Data

Jun. 16, 1998 (SE) .................................. 9802152

(51) Int. Cl.
*A61N 1/365* (2006.01)
(52) U.S. Cl. .......................................... 607/28; 607/11
(58) Field of Classification Search ............... 607/11, 607/27, 28
See application file for complete search history.

(56) References Cited

U.S. PATENT DOCUMENTS

| 4,766,902 A | | 8/1988 | Schroeppel |
| 5,391,192 A | | 2/1995 | Lu et al. |
| 5,431,693 A | | 7/1995 | Schroeppel |
| 5,458,623 A | | 10/1995 | Lu et al. |
| 5,476,487 A | * | 12/1995 | Sholder ........................ 607/28 |
| 5,697,957 A | | 12/1997 | Noren et al. |
| 5,741,312 A | | 4/1998 | Vonk et al. |
| 6,029,088 A | * | 2/2000 | Budgifvars et al. ........... 607/27 |

* cited by examiner

*Primary Examiner*—George Manuel
*Assistant Examiner*—Nicole R. Kramer
(74) *Attorney, Agent, or Firm*—Schiff Hardin LLP

(57) ABSTRACT

A heart stimulator has a pulse generator which emits stimulation pulses of different amplitudes, which are delivered to a patient's heart via a lead connected to the pulse generator. The pulse generator is controlled by a control unit, in a procedure for determining a stimulation threshold value, to emit stimulation pulses of successively unidirectionally changing amplitudes. Each stimulation pulse is followed by a test pulse having a predetermined high, constant amplitude delivered in a period corresponding to the refractory period after the preceding stimulation pulse. Each test pulse has an amplitude sufficient to capture a non-refractory heart. A measurement unit is connected to the electrode lead, and measures a signal picked up by the lead after each test pulse. The measured signals are supplied to a comparator, which compares the signals following the test pulses with each other. A significant change in the measured signal after the test pulses indicates that the amplitude of the stimulation pulses has passed the threshold value.

8 Claims, 2 Drawing Sheets

HEART STIMULATOR WITH EVOKED RESPONSE DETECTOR AND AN ARRANGEMENT FOR DETERMINING THE STIMULATION THRESHOLD

BACKGROUND OF THE INVENTION

1. Field of the Invention

The present invention relates to a heart stimulator having a pulse generator devised for producing stimulation pulses of varying amplitudes, a lead being intended to be introduced into the heart of a patient and connected to the pulse generator for delivering stimulation pulses to the heart.

2. Description of the Prior Art

To reduce the energy consumption of heart stimulators an automatic threshold search function, a so called AUTOCAPTURE™ function, is used to maintain the energy of the stimulation pulses at a level just above that which is needed to effectuate capture, cf. e.g. U.S. Pat. No. 5,458,623. A reliable detection of the evoked response, which then is necessary, is, however, not a simple matter, especially when it is desired to sense the evoked response with the same electrode as the one delivering the stimulation pulse. The reason therefor resides in the fact that the evoked response potential is small in amplitude compared to the residual polarization charge. The residual charge decays exponentially but tends to dominate the evoked potential for several hundreds of milliseconds after the stimulation. If the polarization is too high, it could be wrongly interpreted by the evoked response detector as a capture, i.e. contraction of the heart. The AUTOCAPTURE™ algorithm could then by mistake adjust the output amplitude of the stimulation pulse to a value below the actual capture level, which will result in no capture. If the used pacing lead has significant polarization this could consequently disturb the AUTOCAPTURE™ function and result in loss of capture.

Several attempts have been made to solve the lead polarization problems in connection with evoked response detection. One possibility is to use low polarization leads. This is, however, not always possible.

Another method is described in U.S. Pat. No. 5,417,718, which discloses a system for maintaining capture wherein electrical post-stimulus signal of the heart, following delivery of a stimulation pulse, is compared to a polarization template, determined during a capture verification test. A prescribed difference between the polarization template and the post-stimulus signal indicates capture. Otherwise loss of capture is presumed and the stimulation energy is increased a predetermined amount to obtain capture.

In U.S. Pat. No. 5,697,957 a method and an apparatus for extracting an evoked response component from a sensed cardiac signal by suppressing electrode polarization are descsribed. An autocorrelation function is then calculated according to an autocorrelation algorithm, and is applied to the sensed cardiac signal. The autocorrelated signal thus obtained and the sensed cardiac signal are then normalized to each other and a difference between these two normalized signals is formed, thereby extracting the evoked response component if present in the cardiac signal.

In U.S. Pat. No. 5,741,312 a method and an apparatus are described to determine stimulating threshold through delivery of pulse pairs consisting of a first lower amplitude search pulse with variable amplitude and a second regular pacing pulse within 50–100 ms. Threshold search is executed by incrementing the amplitude of the search pulse until an evoked response is detected. Alternatively the period from regular pacing pulse to the T-wave is measured and capture on the search pulse is determined as a sudden shortening of this interval. U.S. Pat. No. 5,741,312 further discusses methods to minimize polarization by optimizing pulse paramers of a two- or triphasic pacing pulse.

There is mostly at least one significant slope in the bipolar measured IEGM signal, which makes it possible to discriminate the evoked response signal from slowly varying signals such as polarization signals. Thus in U.S. Pat. No. 5,431,693 a method of verifying capture of the heart by a cardiac pacemaker is described. Observing that the non-capture potential is exponential in form and the evoked capture potential, while generally exponential in form, has one or more small-amplitude perturbations superimposed on the exponential wave form, these perturbations are enhanced for ease of detection by processing the wave form signal by differentiation to form the second derivative of the evoked response signal for analysis for the evoked reponse detection.

Unipolar detection of evoked response signals is however not possible by this technique. Abrupt slope changes or superimposed small-amplitude perturbations are levelled out if the measurements are made over a longer distance from the electrode to the stimulator casing.

This is illustrated in FIG. 1 herein, which shows the unfiltered measured electrode signal picked up by a unipolar electrode configuration, the upper curve in the figure, and a bipolar electrode configuration, the lower curve in FIG. 1.

In co-pending United States Application filed simultaneously herewith and identified with International patent application No. PCT/SE99/01017) a new technique is described for solving the polarization problem in connection with evoked response detection. This technique is not based on any slope measurements on the sensed electrode signal, but on determination of the polarization signal for different stimulation amplitudes for then subtracting the polarization signal from the sensed electrode signal to obtain the true evoked response signal. This determination of the polarization is based on the observations that the evoked response signal amplitude is fairly constant, independent of the stimulation pulse amplitude, whereas the electrode polarization is approximately linearly dependent on the stimulation pulse amplitude for a constant pulse duration, cf. European Application 0906768.

The above mentioned manner of determining the polarization presumes that the stimulation threshold value is known.

SUMMARY OF THE INVENTION

An object of the present invention is therefore to provide a technique for determining the stimulation threshold value which is suitable to use in connection with the new way of determining the polarization as described in the aforementioned co-pending patent application.

The above object is achieved in accordance with the principles of the present invention in a heart stimulator having a pulse generator operated by a control unit to emit stimulation pulses of different amplitudes, which are delivered to a patient's heart via an electrode lead connected to the pulse generator. The pulse generator is operated in a procedure to determine the stimulation threshold value to emit stimulation pulses of unidirectionally changing (i.e., decreasing or increasing) amplitudes. Each stimulation pulse is followed by a test pulse having a predetermined high, constant amplitude which is delivered in a period corresponding to the refractory period after the preceding stimulation pulse. The test pulse has an amplitude sufficient to capture a non-refractory heart. A measurement unit is connected to the electrode lead, and measures signals picked up by the electrode lead after each test pulse. The measured signals are provided to a comparator which compares the measured signals following the test pulses with each other. A significant change in the measured signal after the test pulses indicates that the amplitude of the stimulation pulses has passed the threshold value.

Thus with the heart stimulator according to the invention the average amplitudes of the signals following each test pulse are determined, and as long as there is capture on the stimulation pulse, the amplitude of the polarization following the test pulse will show small variations. When the stimulation pulse no longer causes capture, there will be a capture on the test pulse and the amplitude of the following signals will change significantly, thus indicating that the amplitude of stimulation pulse has passed the threshold value. Thus, in this way the threshold value is localized.

The stimulation threshold can be determined before or during the polarization algorithm executed in the evoked response detector according to the aforementioned co-pending International patent application No PCT/SE99/01017, which is an important advantage.

In an embodiment of the heart stimulator according to the invention a calculation unit is provided to calculate the average value of the amplitude of the electrode signal picked up after each test pulse, and the comparator compares the average values with each other to detect significant changes in said average values for use in the determination of threshold value. The measurement unit is preferably adapted to sample and digitize the measured electrode signal during a predetermined time interval after the delivery of the test pulse and the calculation unit is adapted to calculate an average value of said samples. In this way small variations and other interferences in the measured electrode signals are suppressed.

DESCRIPTION OF THE PREFERRED EMBODIMENTS

Figure 1:
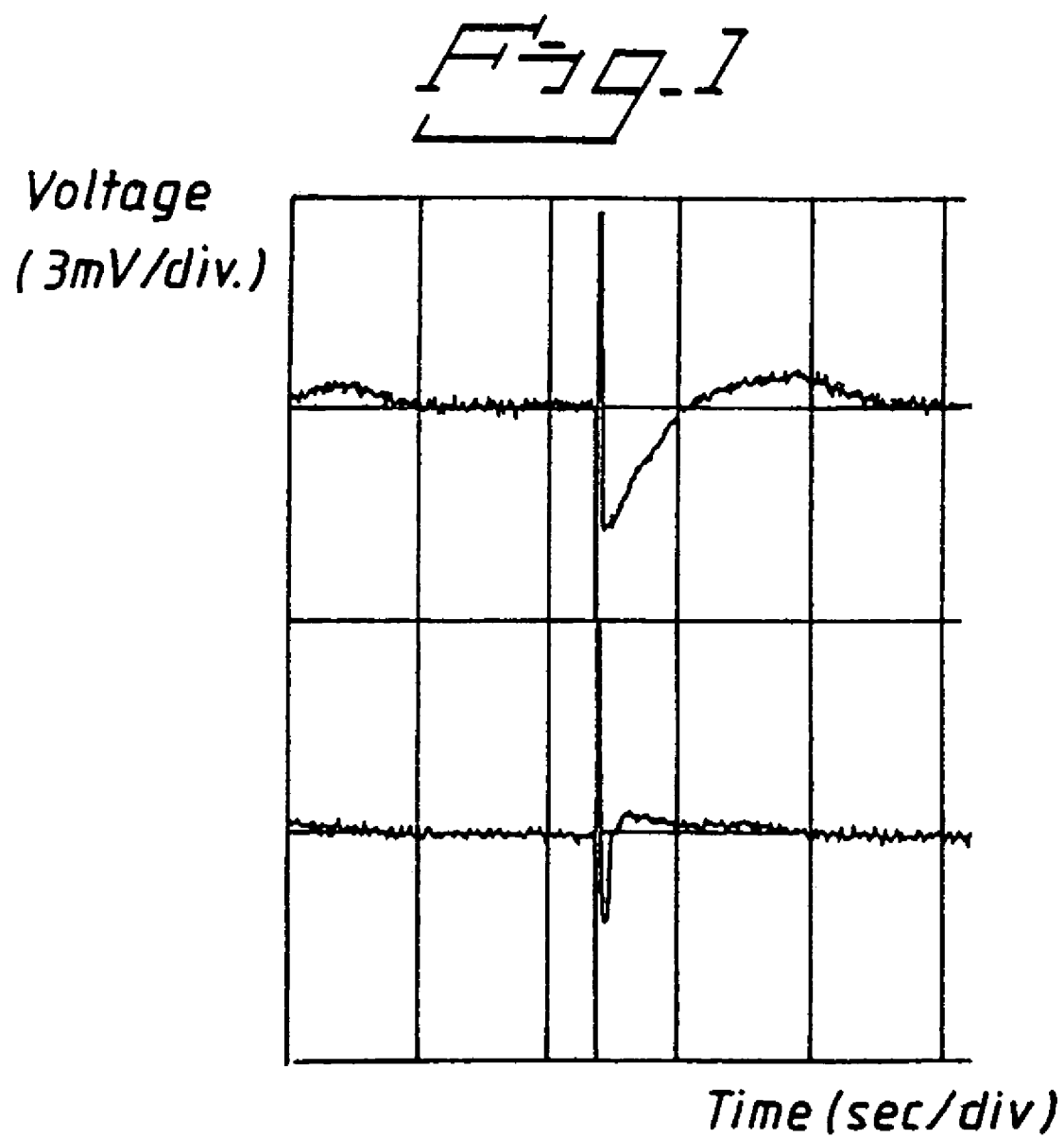
FIG. 1 shows the unfiltered electrode signal measured with a unipolar electrode configuration in the upper curve, with the unfiltered electrode signal measured with a bipolar electrode configuration in the lower curve.
Figure 2:
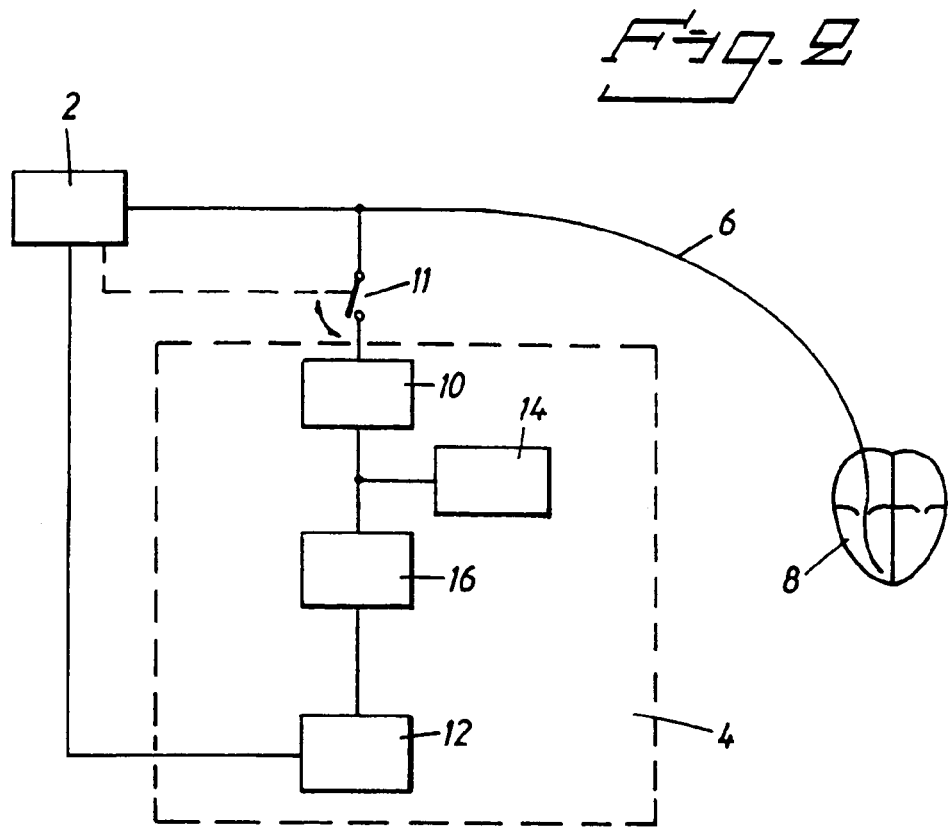
FIG. 2 is a block diagram of a heart stimulator constructed and operating in accordance with the principles of the present invention.

FIG. 2 shows a block diagram of the principal layout of the heart stimulator according to the invention. The stimulator includes a pulse generator 2 which through a lead 6 is connected to the heart 8 of a patient. The pulse generator 2 is devised to produce stimulation pulses of varying amplitudes which through the lead 6 are transferred to the heart 8. An evoked response detector 4 is also connected to the lead 6. The evoked response detector 4 includes a filter and measurement unit 10 for measuring the electrode signal picked up by the lead 6.

The measured electrode signal is supplied to a calculating unit 16 and to a comparator 12 for comparing the measured electrode signals with each other.

The filter and measurement unit 10 is disconnected by the switch 11 from the lead 6 during stimulation.

A timer 14 is provided for determining a time interval after the delivery of the test pulse during which the electrode signal is measured and stored. The measurement unit 10 is adapted to sample and digitize the measured electrode signal during this time interval and the calculation unit 16 calculates an average value of these samples. This average value is then supplied to the means 12 for use in the subsequent comparison step.

As test pulse the ordinary backup pulse of the heart stimulator can preferably be used.

Figure 3:
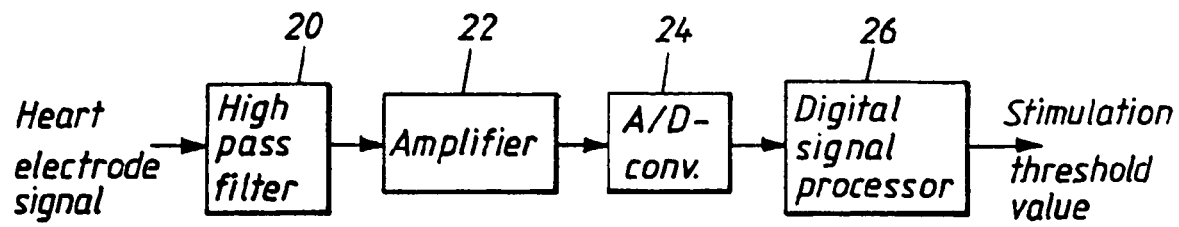
FIG. 3 is a block diagram of an embodiment of an evoked response detector used in the heart stimulator according to the invention.

FIG. 3 shows in more detail an embodiment of the evoked response detector used in the heart stimulator according to the invention. The heart electrode signal picked up by the lead 6 in FIG. 2 is then supplied to a highpass filter 20. An amplifier 22 and an A/D converter 24 are provided for amplifying and A/D converting respectively the filtered signal. A digital signal processor 26 measures, calculates and compares the signals picked up by the lead 6.

Thus in the embodiment shown in FIG. 3 the algorithm for determining the stimulation threshold value is implemented in software by use of a microprocessor. Instead of a microprocessor this algorithm can also be implemented in random logic, which means realization by ordinary logic element, that is logic gates.

The detector can also be implemented in the electronics of the heart stimulator according to the invention by use of switch capacitor (SC) technique. The algorithm is then implemented in SC technique, where different capacitors serve as memory elements for storing the different electrode potentials and SC-adding, subtracting and multiplying circuits are used for performing the necessary calculations.

The function of the embodiment illustrated in FIGS. 2 and 3 is as follows.

Stimulation pulses are delivered in a Vario cycle, i.e. the procedure is started with a stimulation pulse with a high amplitude and then stimulation pulses of successively lower amplitudes are delivered. After each stimulation pulse a test pulse of a high constant amplitude is sent out. This test pulse can preferably be the backup pulse of the heart stimulator in question. The average amplitude of the measured signal after the test pulse is calculated as described above. As long as the delivered stimulation pulses result in capture, the measured electrode signal after the test pulse will be a pure polarization signal, and the average amplitude of these polarization signals will exhibit only small variations as the test pulses have a constant amplitude.

When the amplitude of the stimulation pulse is lowered such that capture is no longer obtained, the test pulse will give rise to capture and the average amplitude of the electrode signal measured after the test pulse will change significantly and become much more negative than the previous signal amplitudes. Thus, this change in the measured signal amplitude indicates that the threshold is passed and the threshold value determined.

If the lowest possible stimulation amplitude is reached, e.g. 0.3 V, and no loss of capture is detected, the average electrode signal following the 0.3 V stimulation pulse is measured and compared with a predetermined value. There are three possible situations explaining the fact that no loss of capture is found, namely 1. The stimulation threshold is below 0.3 V and the absolute average value of the measured signal is larger than the mentioned predetermined value.

2. The stimulation threshold is below 0.3 V and the absolute average value of the measured electrode signal is smaller than the mentioned predetermined value.
3. The stimulation threshold is above 0.3 V, which consequently results in the loss of capture when stimulating with a 0.3 V stimulation pulse, but the absolute average value of the measured electrode signal is smaller than the mentioned predetermined value and therefor cannot be detected after the test pulse.

If the threshold is found and is above 0.3 V or if the situation according to point 1 prevails, the polarization signal $POl_{step}$ for the voltage step of the changing stimulation pulse amplitude can be calculated, either from the cycle of successively changing stimulation pulses already carried through, if the measured electrode signals following the stimulation pulse have been stored, or by starting a new such cycle running down to the threshold amplitude plus one voltage step.

If the threshold is not found and the situation according to point 1 above is not fulfilled, the explanations according to points 2 or 3 must be correct. In that case the measured electrode signal is too low to make a reliable detection of evoked response possible and if the heart stimulator in question is provided with an AUTOCAPTURE™ function it must not be activated.

As an alternative to the above described procedure of successively lowering the stimulation amplitude from a high starting amplitude (Vario cycle), the procedure for determining the threshold can be as follows.

The cycle is started by stimulating a predetermined number of times with a high stimulation amplitude, e.g. 4.5 V, followed by a test pulse equal to a backup pulse of 4.5 V. Then the stimulation amplitude is changed to the lowest possible stimulation amplitude, e.g. 0.3 V, if 0.3 V is the voltage step for the heart stimulator in question, followed by backup pulses of 4.5 V. The average amplitude of the measured polarization signals following the backup pulses are then compared and it is decided whether there was a capture or not after the 0.3 V stimulation pulses according to the above stated criteria. If there was capture, stimulation is performed with stimulation pulses of 4.5 V and then 0.6 V (0.3 V+0.3 V). From the measured electrode signals after the stimulation pulses, which resulted in captures, the $POl_{step}$ signal is calculated.

If there was not a capture for a stimulation amplitude of 0.3 V, the lower stimulation amplitude is increased with the voltage step of 0.3 and the procedure is repeated until the threshold value is reached.

If the stimulation threshold value is above a predetermined value, for both the above described threshold searching methods, the $POl_{step}$ signal can be directly calculatead from the polarization signals measured for stimulation amplitudes below the threshold value.

Although modifications and changes may be suggested by those skilled in the art, it is the intention of the inventors to embody within the patent warranted hereon all changes and modifications as reasonably and properly come within the scope of their contribution to the art.

We claim:

1. A heart stimulator comprising:
    a pulse generator which emits stimulation pulses, each having an amplitude;
    a lead connected to said pulse generator and adapted for introduction into a patient for delivering said stimulation pulses to the patient's heart;
    a control unit connected to said pulse generator for controlling said pulse generator, in a procedure for determining a stimulation threshold value, to emit stimulation pulses of successively unidirectionally changing amplitudes, and a test pulse following each stimulation pulse, each test pulse having a predetermined high, constant amplitude and being delivered in a refractory period after the preceding stimulation pulse, the amplitude of each test pulse being sufficient to capture a non-refractory heart;
    a measurement unit connected to said electrode lead for measuring exclusively an amplitude of electrode signals picked up by said lead after each test pulse, as measured signals; and
    a comparator supplied with said measured signals for comparing the respective amplitudes of said measured signals following each test pulse with each other, and, if a significant change in said amplitude of said measured signals after test pulses occurs, said comparator emitting a signal indicating that the amplitude of the stimulation pulses has passed said stimulation threshold value.

2. A heart stimulator as claimed in claim 1 wherein said control unit controls said pulse generator to emit stimulation pulses of decreasing amplitudes.

3. A heart stimulator as claimed in claim 1 wherein said control unit controls said pulse generator to emit stimulation pulses of increasing amplitudes.

4. A heart stimulator as claimed in claim 1 wherein said control unit controls said pulse generator to deliver stimulation pulses of successively lower amplitudes, beginning with a high pulse amplitude above said stimulation threshold value and wherein said comparator emits said signal if a significant change occurs in the respective amplitudes of said measured electrode signals picked via said lead after said test pulse between two consecutive stimulation pulses, said signal indicating that the amplitude of the stimulation pulses has passed below said threshold value.

5. A heart stimulator as claimed in claim 1 wherein said control unit controls said pulse generator to emit stimulation pulses respectively of first and second different amplitudes, said first amplitude being equal to a highest available stimulation amplitude and said second amplitude being equal to a lowest stimulation amplitude, and wherein said comparator determines if said threshold value is between said first and second amplitudes and, if so, said control unit operates said pulse generator to emit said stimulation pulses with the lowest stimulation amplitude being successive increased by a predetermined step until said threshold value is no longer found by said comparator to be between said stimulation pulses of first and second amplitudes.

6. A heart stimulator as claimed in claim 1 further comprising a calculating unit connected between said measuring unit and said comparator, said calculating unit calculating an average value of the amplitude of the respective measured signals after each test pulse, and supplying said average value to said comparator for use in determining said threshold value.

7. A heart stimulator as claimed in claim 6 wherein said measurement unit samples and digitizes said measured signals during a predetermined time interval after delivery of said test pulse, and wherein said calculating unit calculates said average value from said samples.

8. A heart stimulator as claimed in claim 1 wherein said control unit controls said pulse generator to emit said test pulse as a backup pulse for said pulse generator, having an amplitude of approximately 4.5 V.

* * * * *